US00PP27454P2

(12) United States Plant Patent
Roma

(10) Patent No.: US PP27,454 P2
(45) Date of Patent: Dec. 13, 2016

(54) ***PHEDIMUS* PLANT NAMED 'NONSITNAL'**

(50) Latin Name: *Phedimus takesimense*
Varietal Denomination: Nonsitnal

(71) Applicant: Hortech, Inc., Spring Lake, MI (US)

(72) Inventor: Norberto Miguel Roma, Norton Shores, MI (US)

(73) Assignee: HORTECH, INC., Spring Lake, MI (US)

( * ) Notice: Subject to any disclaimer, the term of this patent is extended or adjusted under 35 U.S.C. 154(b) by 0 days.

(21) Appl. No.: 14/545,980

(22) Filed: Jul. 13, 2015

(51) Int. Cl.
*A01H 5/02* (2006.01)

(52) U.S. Cl.
USPC ..... Plt./263.1

(58) Field of Classification Search
USPC ..... Plt./263.1, 479
CPC ..... A01H 5/02
See application file for complete search history.

*Primary Examiner* — Kent L Bell
(74) *Attorney, Agent, or Firm* — Penny J. Aguirre

(57) ABSTRACT

A new cultivar of *Phedimus* plant, 'Nonsitnal' characterized by its foliage that emerges with light green centers and creamy white edges with the coloration retained throughout summer and fall and dropping the majority of the foliage by winter, its flower buds that are pinkish cream in color, its leaf buds that are cherry red in color, its rounded, upright oriented inflorescences with flowers that are bright canary yellow in color during early summer, and its dense, low growing habit with foliage that reaches 10 cm in height.

2 Drawing Sheets

Botanical classification: *Phedimus takesimense* 'Nonsitnal'.

Variety denomination: 'Nonsitnal'.

BACKGROUND OF THE INVENTION

The present invention relates to a new and distinct cultivar of *Phedimus* plant, botanically known as *Phedimus takesimensis* and will be referred to hereinafter by its cultivar name, 'Nonsitnal'. The new cultivar of *Phedimus* is a hardy herbaceous perennial grown for use as a landscape and container plant and is particularly suitable as a ground cover.

'Nonsitnal' was discovered in July of 2013 as a naturally occurring bud mutation by the Inventor at a nursery in Nunica, Mich. The mutation was found as a single bud mutation of *Phedimus takesimensis* 'Gold Carpet' (not patented) that was growing in a container block of 500 plants of 'Gold Carpet'.

Asexual reproduction of the new cultivar was first accomplished by a single stem cutting in June of 2013. Propagation by stem cuttings has determined the characteristics to be stable and reproduced true to type in successive generations.

SUMMARY OF THE INVENTION

The following traits have been repeatedly observed and are determined to be the characteristics of the new cultivar. These attributes in combination distinguish 'Nonsitnal' as a unique cultivar of *Phedimus*.

1. 'Nonsitnal' exhibits foliage that emerges with light green centers and creamy white edges that is retained throughout summer and fall, and dropping the majority of the foliage by winter.
2. 'Nonsitnal' exhibits flower buds that are pinkish cream in color.
3. 'Nonsitnal' exhibits leaf buds that are cherry red in color.

4. 'Nonsitnal' exhibits rounded, upright oriented inflorescences with flowers that are bright canary yellow in color during early summer.
5. 'Nonsitnal' exhibits a dense, low growing habit with foliage that reaches 10 cm in height.

The parent plant, *Phedimus takesimensis* 'Gold Carpet', differs from 'Nonsitnal' in having a mature foliage canopy height of 15 cm tall (from ground level) and foliage that is colored uniformly green, with no variegation. There are no other known cultivars of *Phedimus takesimensis* known to the Inventor.

BRIEF DESCRIPTION OF THE DRAWINGS

The accompanying colored photographs illustrate the overall appearance and distinct characteristics of the new *Phedimus*. The photographs were taken in July of a 2 year-old plant of 'Nonsitnal' as grown in the ground in full sun in Nunica, Mich.

The photograph in FIG. 1 illustrates the foliage of 'Nonsitnal'.

Figure 1:
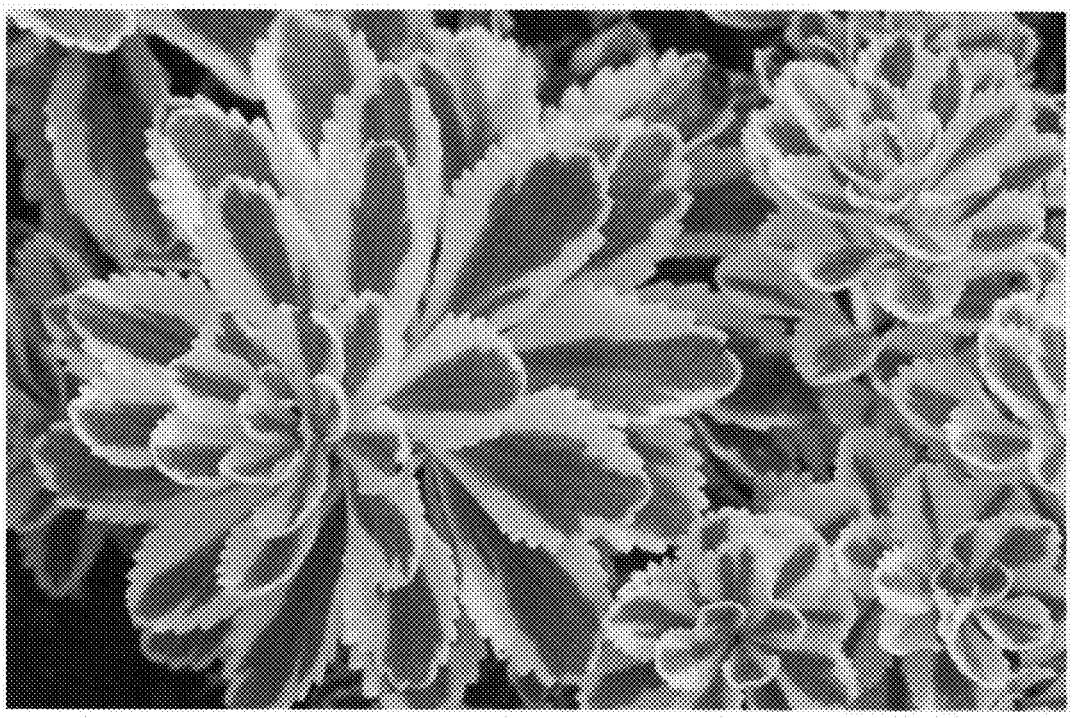
Figure 2:
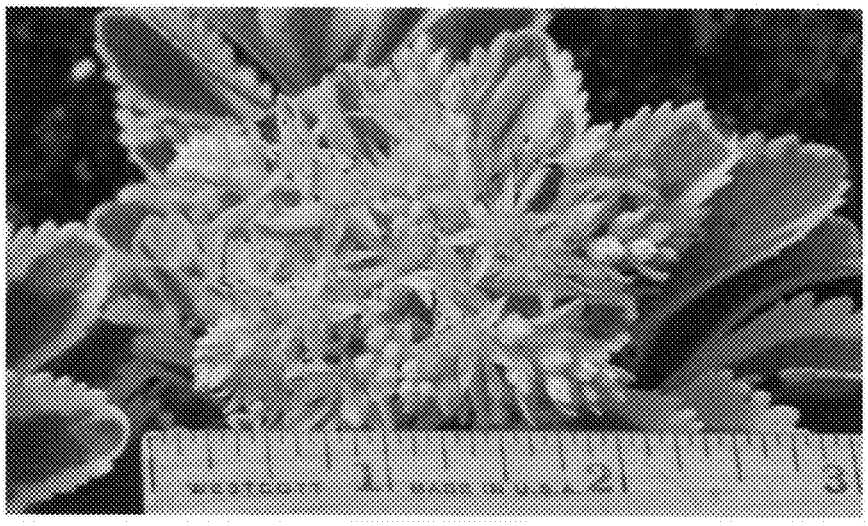

The photograph in FIG. 2 provides a view of the flowers of 'Nonsitnal'.

Figure 3:
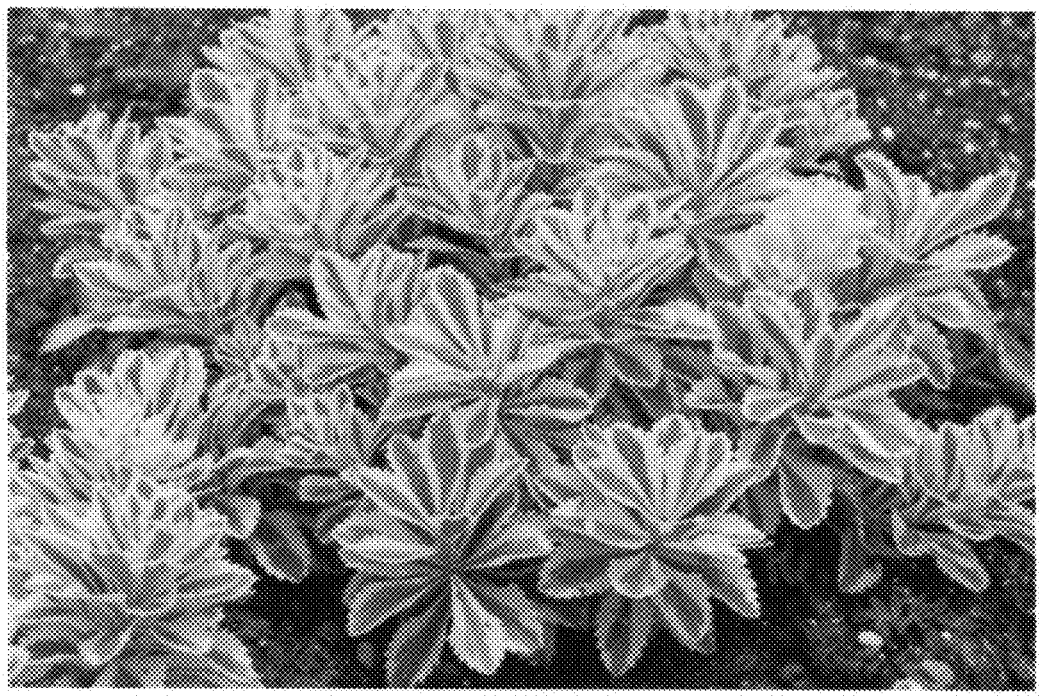

The photograph in FIG. 3 provides a top perspective and illustrates the plant habit of 'Nonsitnal'.

The colors in the photographs may differ slightly from the color values cited in the detailed botanical description, which accurately describe the colors of the new *Phedimus*.

DETAILED BOTANICAL DESCRIPTION

The following is a detailed description of the new cultivar as observed on 2 year-old plants of 'Nonsitnal' as grown in the ground in full sun in Nunica, Mich. The phenotype of the new cultivar may vary with variations in environmental, climatic, and cultural conditions, as it has not been tested under all possible environmental conditions. The color determination is in accordance with The 1986 R.H.S. Colour Chart of The Royal Horticultural Society, London, England, except where general color terms of ordinary dictionary significance are used.

General description:

*Blooming period.*—For 4 weeks in mid summer (in Michigan from July 1 to July 30 approximately).

*Plant type.*—Herbaceous perennial.

*Plant habit.*—Dense, low growing habit.

*Height and spread.*—Reaches about 10 cm in height and about 45 cm in spread.

*Hardiness.*—At least in U.S.D.A. Zones 5 to 9.

*Diseases.*—No particular susceptibility or resistance to diseases has been observed.

*Root description.*—Fibrous, relatively shallow, within 6 cm of soil surface, and colored 161A.

*Propagation.*—Stem cuttings.

*Root development.*—Stem cuttings display root initiation in 7 days when cuttings are stuck in moist soil, takes about 8 weeks for a single stem cutting to develop in a 72-cell plug.

*Growth rate.*—Vigorous.

Stem description:

*Stem shape.*—Round.

*Stem size.*—7 to 10 cm in length and about 3 mm in width.

*Internode length.*—Ranges from 1.5 mm to 6 mm.

*Stem color.*—145B.

*Stem surface.*—Glabrous.

*Branching habit.*—Non branching; branches are basal arising from crown.

Foliage description:

*Leaf shape.*—Spatulate.

*Leaf length.*—40 to 50 mm.

*Leaf width.*—18 to 22 mm.

*Leaf division.*—Simple.

*Leaf arrangement.*—Alternate.

*Leaf base.*—Attenuate.

*Leaf buds.*—Cuspidate, color 39B.

*Leaf apex.*—Obtuse.

*Leaf venation.*—Not conspicuous, color matched leaf color.

*Leaf margins.*—Crenate, young leaves serrate.

*Leaf attachment.*—Sessile.

*Leaf presence and orientation.*—Ascending.

*Leaf surface.*—Glabrous and waxy on upper and lower surface.

*Leaf color.*—Young leaves upper surface; centers 143A, margins 158B, mature leaves upper surface; centers 143C, margins 159C, young leaves lower surface; centers 141C, margins 158B, mature leaf lower surface; centers, margins 186D.

Flower description:

*Inflorescence type.*—Terminal, cymose, upright bud, upright and slightly concave in flower, slightly concave in fruit, branches short and forked, dense many flowered, sparingly leafy.

*Inflorescence size.*—An average of 5 cm in width and 2.5 cm in depth.

*Lastingness of inflorescence.*—About one month.

*Flower type.*—Perfect, spreading, 5-starred.

*Flower number.*—30 to 40 flowers per cyme.

*Flower fragrance.*—None.

*Flower buds.*—Conical in shape, about 3 mm in length and 3 mm in diameter, ribbed surface, 19B in color.

*Flower size.*—About 6 mm length and 10 mm in diameter.

*Peduncles.*—Round, range from 1.5 mm to 3 mm in length, 1.5 mm in width, 160C in color, glabrous surface.

*Pedicels.*—Round, range from 3 mm to 6 mm in length, 3 mm in width, 160C in color, glabrous surface.

*Sepals.*—5, spreading, ovate to lanceolate in shape, about 3 mm in length and 3 mm in width, 158C in color on both surfaces, entire margin, acute apex, truncate base, glabrous surface on both surfaces.

*Petals.*—5, spreading, 3 to 5 mm long by 1.5 to 2 mm wide, lanceolate in shape, truncate base, acute apex, entire margin, color of inner and outer surfaces is 9B, glabrous surfaces on both surfaces.

Reproductive organs:

*Pistils.*—5, held erect, about 10 mm in length, stigma 0.75 mm in width and 150B in color, styles 6.4 cm in length and 150B in color, ovary 2.5 mm in diameter and 150B in color.

*Stamens.*—10, about 10 mm in length, filament 12B in color, anther 7A in color, pollen is sparse in quantity and 7A in color.

*Fruit.*—Rounded with pointed tip, aggregate, range from 1.5 to 3 mm in length and an average of 6 mm in width, 149B in color, seed production was not observed.

It is claimed:

1. A new and distinct variety of *Phedimus* plant named 'Nonsitnal' as described and illustrated herein.

* * * * *